United States Patent
Bodas et al.

(10) Patent No.: US 12,337,307 B2
(45) Date of Patent: Jun. 24, 2025

(54) SYSTEMS, DEVICES, AND METHODS OF A REACTOR FEED DISTRIBUTION SYSTEM

(71) Applicant: SABIC Global Technologies B.V., Bergen op Zoom (NL)

(72) Inventors: Vijay Bodas, Riyadh (SA); Mohammed Ansari, Riyadh (SA); Hua Bai, Sugar Land, TX (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 308 days.

(21) Appl. No.: 17/790,250

(22) PCT Filed: Dec. 30, 2020

(86) PCT No.: PCT/IB2020/062548
§ 371 (c)(1),
(2) Date: Jun. 30, 2022

(87) PCT Pub. No.: WO2021/140411
PCT Pub. Date: Jul. 15, 2021

(65) Prior Publication Data
US 2023/0104851 A1    Apr. 6, 2023

(30) Foreign Application Priority Data
Jan. 7, 2020  (EP) .................................... 20150570

(51) Int. Cl.
*B01J 4/00*     (2006.01)
*B01J 19/24*    (2006.01)
(Continued)

(52) U.S. Cl.
CPC ............. *B01J 4/002* (2013.01); *B01J 19/249* (2013.01); *B01J 19/26* (2013.01); *C07C 5/327* (2013.01);
(Continued)

(58) Field of Classification Search
None
See application file for complete search history.

(56) References Cited

U.S. PATENT DOCUMENTS

| 3,391,869 A | 7/1968 | Glass |
| 3,509,932 A | 5/1970 | Chambers |

(Continued)

FOREIGN PATENT DOCUMENTS

| AU | 2009225514 A1 | 9/2009 |
| BE | 696350 A | 10/1967 |

(Continued)

OTHER PUBLICATIONS

Bar-Meir, Genick. Fundamentals of Compressible Fluid Mechanics, version 0.4.4.2. May 21, 2007. http://www.ibiblio.org/potto/text.pdf, Chapter 5, pp. 81-87.

(Continued)

*Primary Examiner* — Ali Z Fadhel
(74) *Attorney, Agent, or Firm* — Norton Rose Fulbright US LLP

(57) ABSTRACT

Systems, devices, and methods for a reactor feed distribution system. In some aspects, a multi-section pipe and an orifice plate. The multi-section pipe includes a first pipe section that defines a first channel and a second pipe section that defines a second channel. Second pipe section includes a first portion extending along a first longitudinal axis, a second portion extending along a second longitudinal axis that is angularly disposed relative to the first longitudinal axis, and a curved portion connecting the first portion to the second portion. The orifice plate is configured to be positioned at an inlet or a first outlet of the first pipe section. The orifice plate includes a maximum transverse dimension that is less than a minimum transverse dimension of each of the first and second channel.

7 Claims, 3 Drawing Sheets

(51) Int. Cl.
*B01J 19/26* (2006.01)
*C07C 5/327* (2006.01)
(52) U.S. Cl.
CPC .... *B01J 2204/002* (2013.01); *B01J 2204/005* (2013.01)

(56) References Cited

U.S. PATENT DOCUMENTS

| | | | | |
|---|---|---|---|---|
| 3,642,202 | A * | 2/1972 | Angelo | B05B 7/10 239/422 |
| 5,289,976 | A * | 3/1994 | Dou | C10G 11/18 239/431 |
| 5,935,528 | A * | 8/1999 | Stephenson | B01J 8/1827 423/253 |
| 6,193,876 | B1 | 2/2001 | Manolatos et al. | |
| 6,193,936 | B1 * | 2/2001 | Gardner | B01J 19/12 422/186 |
| 6,824,675 | B2 | 11/2004 | Boyer et al. | |
| 10,328,412 | B2 | 6/2019 | Naeemi et al. | |
| 2001/0043888 | A1 * | 11/2001 | Ito | F23D 11/106 422/139 |
| 2002/0153437 | A1 * | 10/2002 | Bouchillon | B04B 1/12 239/223 |
| 2006/0144760 | A1 * | 7/2006 | Duyvesteyn | B01J 8/1827 422/643 |
| 2008/0203196 | A1 | 8/2008 | Laidler et al. | |
| 2009/0266741 | A1 * | 10/2009 | Duyvesteyn | C10G 9/36 422/600 |
| 2010/0298493 | A1 * | 11/2010 | Lipp | B01J 8/1827 526/348 |
| 2012/0063961 | A1 * | 3/2012 | Chan | C10B 55/10 239/398 |
| 2013/0092599 | A1 | 4/2013 | Salazar et al. | |
| 2016/0060541 | A1 * | 3/2016 | Reid | C10J 3/48 422/140 |
| 2017/0211481 | A1 * | 7/2017 | Denton | F16K 1/12 |
| 2018/0031502 | A1 * | 2/2018 | Hutchinson | G01F 15/001 |
| 2018/0154324 | A1 * | 6/2018 | Ganguli | B01J 4/005 |
| 2018/0339280 | A1 * | 11/2018 | Mauro de Feo | B01J 8/0242 |

FOREIGN PATENT DOCUMENTS

| | | |
|---|---|---|
| CA | 665745 A | 6/1963 |
| CA | 2260796 A1 | 1/1998 |
| CN | 104061599 A | 9/2014 |
| DE | 2743124 A1 | 3/1978 |
| EP | 2125177 A1 | 12/2009 |
| EP | 2125177 B1 | 1/2011 |
| GB | 794090 A | 4/1958 |
| KR | 1685056 B1 | 12/2016 |
| KR | 1815752 B1 | 12/2017 |
| WO | WO1996019424 A1 | 6/1996 |
| WO | WO2008077287 A1 | 7/2008 |
| WO | WO2019059928 A1 | 3/2019 |

OTHER PUBLICATIONS

Extended European Search Report from European Application No. 20150570.8 dated Jul. 20, 2020, 9 pages.
International Search Report and Written Opinion from PCT/IB2020/062548 dated Mar. 18, 2021, 13 pages.

* cited by examiner

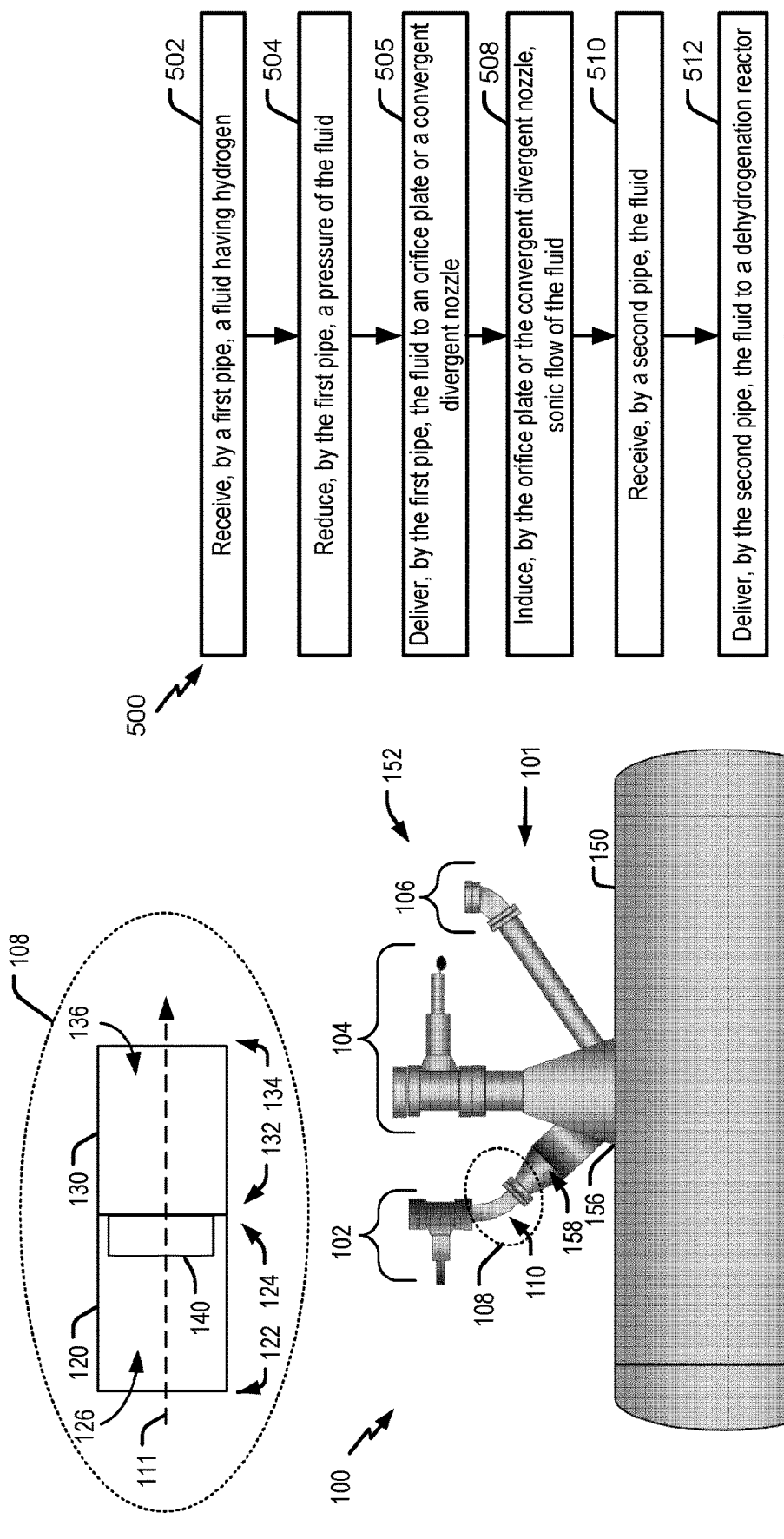

SYSTEMS, DEVICES, AND METHODS OF A REACTOR FEED DISTRIBUTION SYSTEM

CROSS REFERENCE TO RELATED APPLICATIONS

This application is a national phase application under 35 U.S.C. § 371 of International Application No. PCT/IB2020/062548 filed Dec. 30, 2020, which claims priority to European Patent Application No. 20150570.8 filed Jan. 7, 2020. The entire contents of each of the above-referenced disclosures is specifically incorporated by reference herein without disclaimer.

TECHNICAL FIELD

The present disclosure relates generally to inlet piping for use in a reactor, and more specifically, but not by way of limitation, to a hydrocarbon feed inlet of a dehydrogenation reactor.

BACKGROUND

A critical flow orifice is typically positioned upstream of a dehydrogenation reactor to create sonic flow into the dehydrogenation reactor. Sonic flow enables control of a system by altering flow upstream of a critical flow orifice regardless of downstream pressure changes. While a sonic flow orifice enables control of the flow rate of the system, use of a sonic flow orifice(s) can also generate significant pressure drops (e.g. up to 90%) and temperature loss in the system. To maintain operation temperatures (e.g., 500° C. and above) for the highly endothermic dehydrogenation process, extra energy is used to counteract the loss of temperature and pressure at the critical flow orifice. For example, a conventional approach increases the exit temperature of a heater positioned upstream of one or more reactors. However, the conventional approach is not energy efficient and increases the operational cost of the reactor.

SUMMARY

The present disclosure is generally related to systems, devices, and methods of a reactor feed distribution system. For example, a system may include one or more sections of pipe and an orifice plate. The orifice plate is configured and/or positioned to induce sonic flow within the system, prevent energy loss, or both. To illustrate, the one or more sections of pipe may include a single pipe section or a multi-section pipe having a first pipe section, a second pipe section, and the orifice plate. The orifice plate may be positioned at an inlet or an outlet of a pipe section. When one or more sections include a multi-section pipe, the orifice plate may be positioned at an inlet or an outlet of a first pipe section and may have a maximum transverse dimension that is less than a minimum transverse dimension of each channel of the first and second pipe sections. In some implementations, the first pipe section may include a nozzle portion, a throat portion, a diffuser portion, or a combination thereof. Additionally, or alternatively, the second pipe section may include a first portion, a second portion, and a curved portion that cooperate to reduce or limit pressure loss in the multi-section pipe. Consequentially, as compared to a conventional system, the present disclosure, including one or more sections of pipe and an orifice plate, provides for an energy efficient system for minimizing thermodynamic loss at an inlet of a dehydrogenation system both in terms of temperature and pressure loss.

Some implementations of the present systems include a multi-section pipe and an orifice plate. The multi-section pipe includes a first pipe section and a second pipe section. The first pipe section defines a first channel configured to convey fluid from a first inlet of the first pipe section to a first outlet of the first pipe section. The second pipe section defines a second channel configured to convey fluid from a second inlet of the second pipe section to a second outlet of the second pipe section. The second pipe section includes a first portion extending along a first longitudinal axis, a second portion extending along a second longitudinal axis that is angularly disposed relative to the first longitudinal axis, and a curved portion connecting the first portion to the second portion. The orifice plate is configured to be positioned at the first inlet or the first outlet. The orifice plate includes a maximum transverse dimension that is less than a minimum transverse dimension of each of the first and second channel.

In some of the foregoing implementations, the curved portion of the second pipe section includes a deflection angle that is less than 60 degrees (e.g., 45.5 degrees) or angle of the standard Long radius elbow. Additionally, or alternatively, in some implementations, the orifice plate is positioned at the first outlet. In some such implementations the system further includes a dehydrogenation reactor and the multi-section pipe is positioned upstream of the dehydrogenation reactor such that a flow path is defined from the first pipe section, through the orifice plate, through the second pipe section, to an inlet of the dehydrogenation reactor. In some implementations, the first pipe section includes a hot-wall pipe, the second pipe section includes a hot-wall pipe, or both. Additionally, or alternatively, the first pipe section may be tapered such that the first channel increases in cross-sectional area as the first channel extends from the first inlet to the first outlet.

Some implementations of the present systems include inlet piping for a reactor. The inlet piping includes a multi-section pipe. The multi-section pipe includes a first pipe having an inlet and an outlet and defining a channel configured to convey fluid from the inlet to the outlet to define a flow path of the first pipe. The first pipe includes a nozzle portion, a divergent portion, and a throat portion. The nozzle portion extends from the inlet and includes a taper that decreases a cross-sectional area of the channel from an upstream end of the nozzle portion to a downstream end of the nozzle portion. The divergent portion extends from the outlet and includes a taper that increases the cross-sectional area of the channel from an upstream end of the diffuser portion to a downstream end of the diffuser portion. The throat portion extends between the downstream end of the nozzle portion and the upstream end of the diffuser portion. The multi-section pipe includes a second pipe in fluid communication with the first pipe. In some implementations, the inlet piping further includes an orifice plate. The orifice plate may be coupled to the downstream end of the diffuser portion.

In some of the foregoing implementations of the present systems, an inner diameter of the channel at the throat portion is substantially equal to the inner diameter of the channel at the downstream end of the nozzle portion. Additionally, or alternatively, an inner diameter of the channel is substantially constant in the throat portion. In some implementations, the first pipe includes a hot-wall pipe, the second pipe includes a hot-wall pipe, a distance between the inlet of the first pipe and the reactor is between 10-15 meters, or a combination thereof.

Some implementations include a plurality of dehydrogenation reactors arranged in parallel and in communication with the multi-section pipe. In some such implementations, the multi-section pipe is positioned upstream of the plurality of dehydrogenation reactors such that a flow path is defined from the first pipe, through an orifice plate or a convergent-divergent nozzle, through the second pipe, to an inlet of the dehydrogenation reactor. Additionally, or alternatively, the orifice includes a maximum transverse dimension that is less than a minimum transverse dimension of the channel and/or the second pipe includes an elbow pipe with a deflection angle that is less than or equal to 50 degrees.

Some implementations of the present methods (e.g., of performing a dehydrogenation process) include receiving, by a first pipe, a fluid having hydrogen, reducing, by the first pipe, a pressure of the fluid, and delivering, by the first pipe, the fluid to an orifice plate or a convergent-divergent nozzle. The present methods further include inducing, by the orifice plate or the convergent-divergent nozzle, sonic flow of the fluid, receiving, by a second pipe, the fluid, and delivering, by the second pipe, the fluid to a dehydrogenation reactor.

In some of the foregoing implementations of the present methods, the methods may further include, prior to reducing the pressure of the fluid by the first pipe, compressing the fluid by the first pipe. Additionally, or alternatively, the methods may also include creating, by the second pipe, an oblique shock in the fluid. In some implementations, delivering the fluid to the dehydrogenation reactor includes delivering the fluid to a plurality of dehydrogenation reactors that is positioned in parallel. Additionally, or alternatively, in some of the foregoing methods, the fluid includes an alkane. In some such implementations, the method may include converting the alkane to an alkene, by the dehydrogenation reactor.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed implementations, the term "substantially" may be substituted with "within [a percentage] of" what is specified, where the percentage includes 0.1, 1, 5, and 10 percent.

The term "about" as used herein can allow for a degree of variability in a value or range, for example, within 10%, within 5%, or within 1% of a stated value or of a stated limit of a range and includes the exact stated value or range. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed implementation, the term "substantially" may be substituted with "within [a percentage] of" what is specified, where the percentage includes 0.1, 1, or 5 percent; and the term "approximately" may be substituted with "within 10 percent of" what is specified. The statement "substantially X to Y" has the same meaning as "substantially X to substantially Y," unless indicated otherwise. Likewise, the statement "substantially X, Y, or substantially Z" has the same meaning as "substantially X, substantially Y, or substantially Z," unless indicated otherwise. The phrase "and/or" means and or or. To illustrate, A, B, and/or C includes: A alone, B alone, C alone, a combination of A and B, a combination of A and C, a combination of B and C, or a combination of A, B, and C. In other words, "and/or" operates as an inclusive or. Additionally, the phrase "A, B, C, or a combination thereof" or "A, B, C, or any combination thereof" includes: A alone, B alone, C alone, a combination of A and B, a combination of A and C, a combination of B and C, or a combination of A, B, and C.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those one or more elements. Likewise, a method that "comprises," "has," or "includes" one or more steps possesses those one or more steps, but is not limited to possessing only those one or more steps.

In the context of the present invention at least fifteen embodiments are now described. Embodiment 1 is an inlet feed system for a reactor. The inlet feed system includes a multi-section pipe having a first pipe section defining a first channel configured to convey fluid from a first inlet of the first pipe section to a first outlet of the first pipe section; and a second pipe section defining a second channel configured to convey fluid from a second inlet of the second pipe section to a second outlet of the second pipe section. The second pipe section includes a first portion extending along a first longitudinal axis; a second portion extending along a second longitudinal axis that is angularly disposed relative to the first longitudinal axis; and a curved portion connecting the first portion to the second portion; and an orifice plate configured to be positioned at the first inlet or the first outlet, the orifice plate includes a maximum transverse dimension that is less than a minimum transverse dimension of each of the first and second channel. Embodiment 2 is the system of embodiment 1, wherein the curved portion of the second pipe section includes a deflection angle less than 60 degrees; or the orifice plate is positioned at the first outlet; and optionally, the first pipe section includes a hot-wall pipe, the second pipe section includes a hot-wall pipe, or both. Embodiment 3 is the system of any of embodiments 1-2, further including a dehydrogenation reactor; and wherein the multi-section pipe is positioned upstream of the dehydrogenation reactor such that a flow path is defined from the first pipe section, through the orifice plate, through the second pipe section, to an inlet of the dehydrogenation reactor; or wherein the first pipe section is tapered such that the first channel increases in cross-sectional area as the first channel extends from the first inlet to the first outlet.

Embodiment 4 is an inlet piping for a reactor. The inlet piping includes a multi-section pipe including a first pipe comprising an inlet and an outlet, the first pipe defining a channel configured to convey fluid from the inlet to the outlet, to define a flow path of the first pipe, the first pipe including a nozzle portion extending from the inlet, the nozzle portion having a taper that decreases a cross-sectional area of the channel from an upstream end of the nozzle portion to a downstream end of the nozzle portion; a diffuser portion extending from the outlet, the diffuser portion having a taper that increases the cross-sectional area of the channel from an upstream end of the diffuser portion to a downstream end of the diffuser portion; and a throat portion extending between the downstream end of the nozzle portion and the upstream end of the diffuser portion; and a second pipe in fluid communication with the first pipe. Embodiment 5 is the inlet piping of embodiment 4, wherein an inner diameter of the channel at the throat portion is substantially equal to the inner diameter of the channel at the downstream end of the nozzle portion. Embodiment 6 is the inlet piping of any of embodiments 4-5, wherein an inner diameter of the channel is substantially constant in the throat portion. Embodiment 7 is the inlet piping of any of embodiments 4-6, wherein the first pipe includes a hot-wall pipe. Embodiment 8 is the inlet piping of embodiment 7, wherein the second pipe includes a hot-wall pipe. Embodiment 9 is the inlet piping of any of embodiments 4-8, wherein a distance between the inlet of the first pipe and the reactor is between 10-15 meters. Embodiment 10 is the inlet piping of any of embodiments 4-9, further including a plurality of dehydrogenation reactors arranged in parallel, each dehydrogenation reactor in communication with the multi-section pipe; and wherein the multi-section pipe is positioned upstream of the plurality of dehydrogenation reactors such that a flow path is defined from the first pipe, through an orifice plate or a convergent-divergent nozzle, through the second pipe, to an inlet of the dehydrogenation reactor. Embodiment 11 is the inlet piping of embodiment 10, wherein the orifice plate includes a maximum transverse dimension that is less than a minimum transverse dimension of the channel. Embodiment 12 is the inlet piping of embodiments 4 to 11, wherein the second pipe includes an elbow pipe with a deflection angle that is less than or equal to 50 degrees.

Embodiment 13 is a method of performing a dehydrogenation process, the method includes receiving, by a first pipe, a fluid having hydrogen; reducing, by the first pipe, a pressure of the fluid; delivering, by the first pipe, the fluid to an orifice plate or a convergent-divergent nozzle; inducing, by the orifice plate or the convergent-divergent nozzle, sonic flow of the fluid; receiving, by a second pipe, the fluid; delivering, by the second pipe, the fluid to a dehydrogenation reactor. Embodiment 14 is the method of embodiment 13, further including prior to reducing the pressure of the fluid by the first pipe, compressing the fluid by the first pipe; or creating, by the second pipe, an oblique shock in the fluid. Embodiment 15 the method of any of embodiments 13 to 14, wherein delivering the fluid to the dehydrogenation reactor includes delivering the fluid to a plurality of dehydrogenation reactors disposed in parallel; or the fluid includes an alkane and the method further comprising converting the alkane to an alkene, by the dehydrogenation reactor.

Any implementation of any of the systems, methods, and article of manufacture can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, the term "wherein" may be used interchangeably with "where". Further, a device or system that is configured in a certain way is configured in at least that way, but it can also be configured in other ways than those specifically described. The feature or features of one implementation may be applied to other implementations, even though not described or illustrated, unless expressly prohibited by this disclosure or the nature of the implementations.

Some details associated with the implementations are described above, and others are described below. Other implementations, advantages, and features of the present disclosure will become apparent after review of the entire application, including the following sections: Brief Description of the Drawings, Detailed Description, and the Claims.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 1 is a side view of an example of a dehydrogenation system including a reactor.

FIG. 2A is a cross-sectional view of an example of an inlet assembly.

FIG. 2B is a cross-sectional view of another example an inlet assembly.

FIG. 5 is a flowchart of a method of performing a dehydrogenation process.

DETAILED DESCRIPTION

Figure 4A:
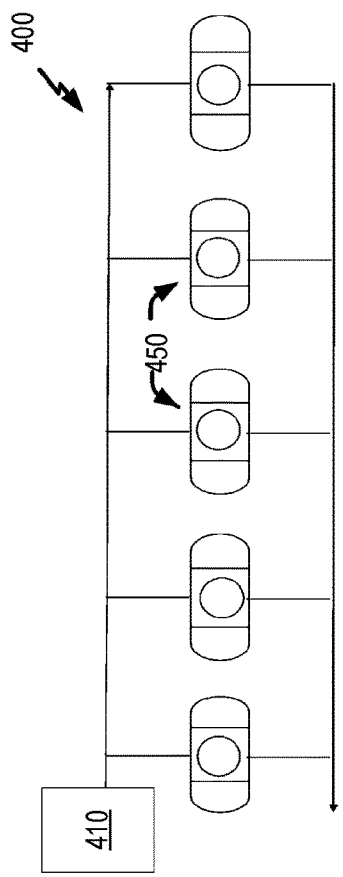
FIGS. 4A and 4B are illustrative examples of systems including multiple reactors.

Referring to FIG. 1, a side view of an example a dehydrogenation system including a reactor is shown and designated 100. System 100 may be configured to reduce pressure and temperature loss associated with a feed inlet of a reactor 150. Reactor 150 may define a body having a chamber in which a reaction (e.g., chemical reaction) occurs. In some implementations, reactor 150 includes a fixed bed catalytic reactor. Reactor 150 includes an inlet one or more inlets 152 and one or more outlets 154. Reactor 150 may define a portion of a flow path of system 100 from inlet 152, through the reaction chamber, to outlet 154. In some implementations, reactor 150 also includes a port 156 coupled to the inlets 152 and/or outlets 154, and configured to receive or deliver a fluid of the system 100 to or from one or more other components. For example, port 156 may enable reactor 150 to be in fluid communication with one or more other components of system 100, as described herein. Additionally, or alternatively, reactor may include piping 158 (e.g., reactor piping or cactus piping) that may connect an inlet 152 to port 156 in certain configurations.

System 100 includes one or more inlet paths (e.g., cactus piping 101) configured to each deliver a fluid to reactor 150. For example, system 100 may include a first inlet 102, a second inlet 104, and a third inlet 106. Each inlet may be configured to deliver a separate fluid to reactor 150. For example, first inlet 102 may transport a hydrocarbon feed, such as Propane, n-Butane, IsoButane, IsoPentane, or the like, as illustrative, non-limiting examples, second inlet 104 may be configured to transport air, and third inlet 106 may be configured to transport a reduction gas or steam. In some implementations, inlets 102, 104, 106 may be arranged in a cactus orientation such that one or more pipes converge at a port of reactor 150. For example, first and third inlet 102, 106 are angularly disposed relative to second inlet 104 in a cactus configuration to improve mixture of the fluids entering reactor 150. System 100 may also include one or more outlet paths that transport a fluid away from reactor 150. In some implementations, system 100 may include a compressor 105 that is configured to increase or decrease a flow rate of system 100. As shown, compressor 105 is positioned downstream of reactor 150, however, in some implementations, compressor 105 may be or include an upstream feed pump, a downstream compressor, or both.

At least one of the inlets (e.g., 102) includes a feed inlet assembly (e.g., assembly 110) positioned upstream of reactor 150 to define a portion of a flow path of system 100. For example, assembly 110 is positioned upstream of reactor 150 such that a fluid travels through assembly 110 to reactor 150. Assembly 110 and reactor 150 may be coupled together in any suitable manner such as, one or more fasteners (e.g., blots, screws, rivets, or the like), welded, friction, other intervening parts, or the like. As an illustrative, non-limiting example, assembly 110 is coupled to reactor piping 158. Piping 158 may provide a portion of the flow path from an inlet (e.g., 102) to reactor 150. For example, a fluid may be transported from inlet assembly 110 to piping 158, to port 156, to reactor 150. To illustrate, piping 158 may include or correspond to cactus piping 101. In some implementations, system 100 includes one or more additional components, such as one or more pumps, compressors, heaters, gravity separators, turbines, valves, catalysts, a combination thereof, or the like, as illustrative, non-limiting example, which are not shown for convenience.

Assembly 110 includes one or more pipes configured to convey a fluid, such as a hydrocarbon feed, to reactor 150. Although referred to herein as assembly 110, assembly 110 may also be referred to herein as feed assembly, inlet assembly, feed piping, inlet piping, feed inlet, feed inlet system, or inlet feed system. Assembly 110 may be configured to adequately distribute the flow of the fluid as well as minimize thermodynamic loss of the system. In some implementations, assembly 110 may a hot-wall design and/or a cold-wall design.

A block diagram of an example of one of the inlet pipes (e.g., hydrocarbon feed inlet) is shown at 108. Although assembly 110 is shown and described with reference to the hydrocarbon feed inlet, assembly 110 may be utilized on one or more other inlet pipes of reactor 150, such as air inlet (e.g., 104), reduction gas inlet (e.g., 106), or both. As shown at 108, assembly 110 includes a first pipe 120, a second pipe 130, and an orifice 140 (e.g., an orifice plate). First pipe 120, second pipe 130, and orifice 140 may be coupled together to define a portion of the flow path of system 100. For example, the portion 111 of a flow path of system 100 may be defined from first pipe 120, to orifice 140, to second pipe 130. To illustrate, pipes 120, 130 and orifice 140 are each configured to transport a fluid through a respective portion of flow path 111. Additionally, the flow path of system 100 may at least be defined from first pipe 120 through second pipe 130 to reactor 150. Although first pipe 120 and second pipe 130 are described and depicted as separate components, first and second pipes 120, 130 may be unitary such that first pipe 120 corresponds to a first portion of a pipe and second pipe 130 corresponds to a second portion of the pipe.

Figures 2A, 2B:
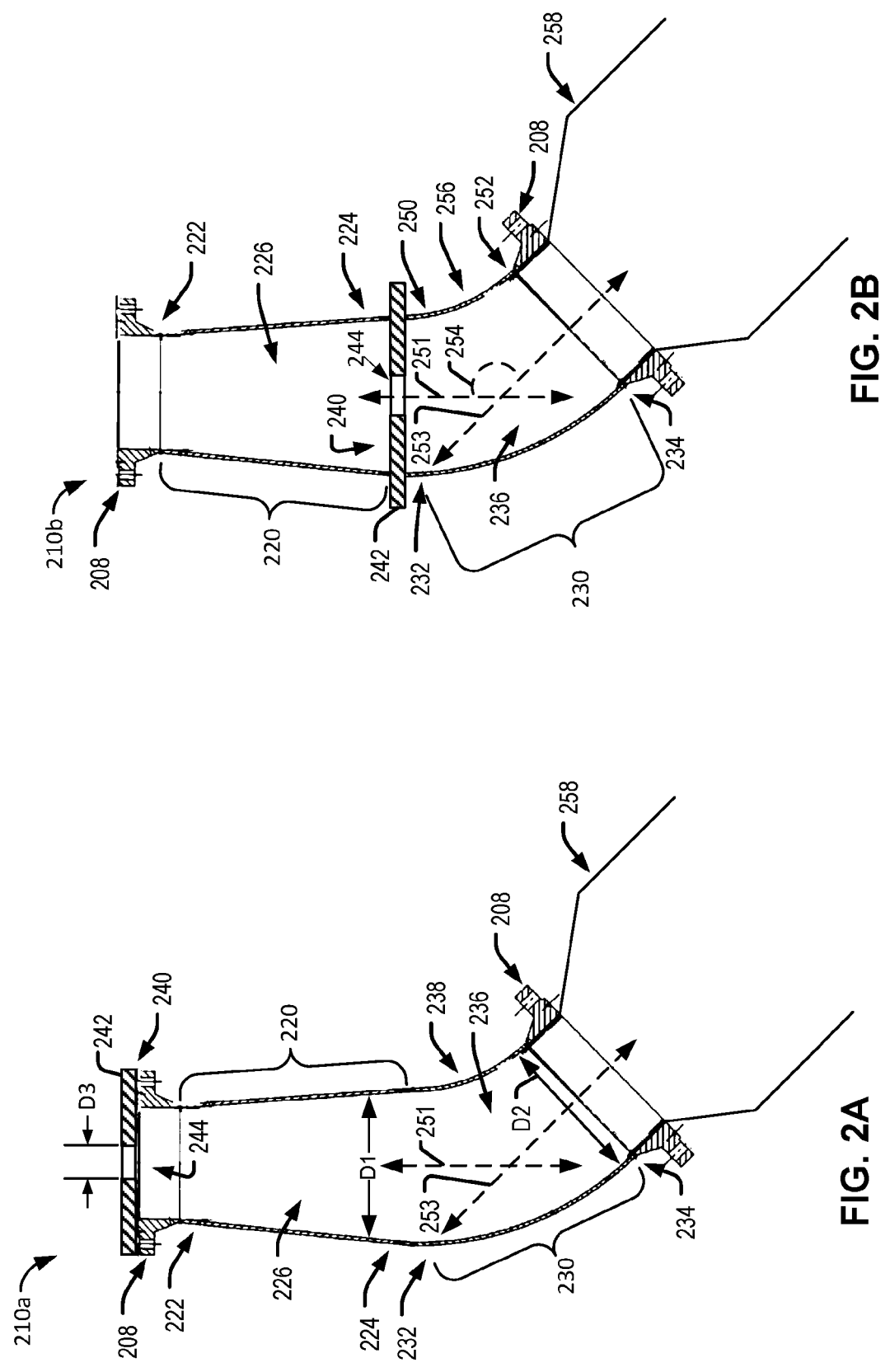

First pipe 120 includes a first end 122 and a second end 124. As shown, first end 122 is opposite of second end 124. First pipe 120 may transport a fluid (e.g., liquid, gas, or combination thereof) from first end 122 to second end 124. First pipe 120 includes one or more walls that define a channel 126 that extends between first end 122 and second end 124 to convey a fluid (e.g., hydrocarbon feed). As shown, first pipe 120 may be coupled to one or more other components (e.g., second pipe 130 and/or orifice 140) of assembly 110. Additionally, or alternatively, first pipe section 120 may include one or more features, such as, a nozzle portion, a throat portion, a divergent portion, or other features, as described further herein with reference to FIGS. 2A, 2B, and 3.

Second pipe 130 includes a first end 132 and a second end 134. As shown, first end 132 is opposite second end 134. Second pipe 130 includes one or more walls that define a channel 136 that extends between first end 132 and second end 134 to convey a fluid (e.g., hydrocarbon feed). In some implementations, second pipe 130 may include one or more features, such as a first portion extending along a first longitudinal axis, a second portion extending along a second longitudinal axis that is angularly disposed relative to the first longitudinal axis, and a curved portion connecting the first portion to the second portion, as described further herein at least with reference to FIGS. 2A, 2B, and 3. As shown in FIG. 1, second pipe 130 is positioned downstream of first pipe 120 to define a flow path of inlet assembly 120. For example, first end 132 of second pipe 130 is coupled to second end 124 of first pipe 120. In some implementations, one or more intervening components may be positioned between first pipe 120 and second pipe 130. Additionally, or alternatively, second pipe 130 may be coupled to reactor 150. For example, second end 134 of second pipe 130 may be coupled to reactor 150 (e.g., port 156 of the reactor).

Orifice 140 is configured to induce sonic flow within system 100 downstream of orifice 140 during operation of system 100. To illustrate, orifice 140 (e.g., orifice plate) may restrict fluid flow (e.g., reduce pressure) such that mass flow of system 100 may be controlled independently of pressure variations downstream of orifice 140. For example, orifice 140 may define a vena contracta of system 100, such as a portion of system 100 where diameter of the flow path of system 100 is at a minimum, and fluid velocity is at its maximum. As shown, orifice 140 is positioned within channel 126 at second end 124 of pipe 120. In other implementations, orifice 140 may be positioned at any location within channel 126 of pipe 120 and/or channel 136 of pipe 130, as described further herein. In some implementations, orifice 140 may be coupled to pipe 120 or pipe 130 outside of channels 126, 136. For example, orifice 140 may be positioned within, or coupled to, pipe 120. To illustrate, orifice 140 may be coupled to pipe 120 at first end 122, second end 124, or between ends 122, 124. Orifice 140 may configured to attain sonic flow at a percentage of startup feed flow of system 100. To illustrate, orifice 140 may configured to attain sonic flow of at least 75% (e.g., 80%) of startup feed flow of system 100, as an illustrative, non-limiting example.

During operation, one or more fluids are transported through each inlet (e.g., 102, 104, 106) to reactor 150 where at least one of the fluids may undergo a chemical reaction (e.g., dehydrogenation). Inlets (e.g., 102, 104, 106) may deliver a corresponding fluid to reactor 105 to enable a chemical reaction. For example, a first fluid in first inlet 102 may be introduced at first pipe 120 through second pipe 130 and into reactor 150 during operation. Additionally, the first fluid may flow through orifice 140 to create sonic flow of the first fluid downstream of the orifice as the first fluid enters reactor 150. As the first fluid passes through assembly 110, the first fluid may be under sonic conditions without creating a large pressure of temperature drop. Typically, decreased velocity associated with a small pressure drop is undesired in dehydrogenation processes as it is known that conversion in the reactor (e.g., 150) is inversely related to pressure. However, the energy conservation from the decreases thermodynamic loss of the first fluid through assembly 110 may compensate for the adverse impact on conversion in reactor 150. For example, a compressor capability of compressor 105 may increase super-linearly (e.g., due to compressor pressure drop being a function of the square of flow) and the increase in compressor suction pressure may outweigh the drop in conversion up to a certain point (e.g., stonewall limit) so that assembly 110 increases the efficiency of system 100 despite any decreased conversion rate. After the chemical reaction of system 100, an output is provided via one or more outlets 154.

Orifice 140 may be positioned within system 100 to increase the pressure drop and velocity of fluid (e.g., 112) through a reactor (e.g., 150). For example, positioning orifice 140 closer to end 122 of first pipe 120 may produce increase the pressure drop and velocity of fluid (e.g., 112) through the reactor as compared to positioning orifice 140 closer to second end 124. Accordingly, orifice 140 may be positioned relative to first end 122 of first pipe 120, second end 124 of the first pipe, first end 132 of second pipe 130, a bend of the second pipe, or other feature to maximize efficiency of the system (e.g., 100) based on a compressor or reactor type.

Assembly 110 may be sized and shaped based on one or more operation parameters (e.g., fluid type, number of reactors, flow rate, etc.) of system 100, such as a dehydrogenation system, to minimize thermodynamic loss of the system. In some implementations, assembly 110 may include a first portion that is hot-wall design and a second portion that is cold-wall design. For example, in a non-limiting implementation, first pipe 120 may correspond to a hot-wall pipe and second pipe 130 may, but need not, correspond to a cold-wall pipe. When first pipe 120 corresponds to the hot-wall pipe, first pipe 120 may include a hot-wall design (e.g., a hot-wall pipe) such that first pipe 220 is externally heated. In some such implementations, first pipe 120 does not include refractory lining. In another example, first pipe 120 and second pipe 130 may correspond to a hot-wall pipe and, optionally, one or more components downstream of the first and second pipe may correspond to a cold-wall design.

In some implementations, system 100 includes assembly 110, such as a multi-section pipe, that includes a first pipe section (e.g., 120) defining a first channel 126 configured to convey fluid from a first inlet (e.g., at 122) of the first pipe section to a first outlet (e.g., at 124) of the first pipe section and a second pipe section (e.g., 130) defining a second channel 136 configured to convey fluid from a second inlet (e.g., at 132) of the second pipe section to a second outlet (e.g., at 134) of the second pipe section. The second pipe section may include a first portion extending along a first longitudinal axis, a second portion extending along a second longitudinal axis that is angularly disposed relative to the first longitudinal axis, and a curved portion connecting the first portion to the second portion, as described further herein with reference to FIGS. 2A, 2B, and 3. In some such implementations, system 100 includes orifice plate 140 which may be positioned at the first inlet (e.g., 122) or the first outlet (e.g., 124). In at least some of the foregoing implementations, orifice plate 140 includes a maximum transverse dimension that is less than a minimum transverse dimension of each of the first (e.g., 126) and second channel (e.g., 136).

System 100 advantageously includes pipes 120, 130 and orifice 140 configured to cooperate to minimize thermodynamic loss from temperature and pressure drops in assembly 110 as compared to traditional feed inlets. In such implementations, the pressure drop and the mass flow of a fluid through system 100 may be minimized, as described herein, in a manner that is not possible in conventional cold-wall design systems that suffer from failures of refractory lining in the sonic flow area. In some implementations, system 100 includes a multi-section pipe for a hydrocarbon feed inlet of a dehydrogenation reactor to prevent energy loss from significant pressure and temperature loss in inlet orifices. For example, assembly 110 may generate sonic flow through an inlet (e.g., 102) so that the flow of a fluid can be controlled independent of downstream pressure drops or variation associated with dehydrogenation reactors so that an equal amount of fluid is distributed to each reactor. Additionally, assembly 110 minimizes thermodynamic loss (e.g., pressure and temperature) of the sonic fluid to create a more efficient reaction process, while still maintaining flow distribution of the fluid through one or more reactors in the system.

Referring FIGS. 2A-2B, examples of inlet assemblies of a system, such as a dehydrogenation system, are shown. FIG. 2A shows a cross-sectional view of a first example of an inlet assembly 210a, and FIG. 2B shows a cross-sectional view of a second example of an inlet assembly 210b. Inlet assembly 210a, 210b may include or correspond to assembly 110. In some implementations, assembly 210a, 210b may be configured to provide improved energy efficiency for pipe flow in a dehydrogenation system, such as system 100.

Referring to FIGS. 2A-2B, assembly 210a and 210b includes a first pipe 220, a second pipe 230, and an orifice 240. First pipe 220, second pipe 230, and orifice 240 may include or correspond to first pipe 120, second pipe 130, and orifice 140, respectively. First pipe 220 extends from a first end 222 to a second end 224 and defines a channel 226 between first end 222 and second end 224. First end 222, second end 224, and channel 226 may include or correspond to first end 122, second end 124, and channel 126, respectively. As shown, first pipe 220 includes a first distance D1 (e.g., diameter) that defines a transverse dimension of channel 226 taken along a plane orthogonal the longitudinal axis of channel 226. First distance D1 may be measured from opposing sides of inner surface of first pipe 220. In some implementations, first distance D1 corresponds to a diameter of channel 226. For example, D1 may be a maximum transverse dimension, such as a maximum transverse inner diameter of first pipe 220. To illustrate, the maximum transverse inner diameter of first pipe 220 may be located at second end 224.

In some implementations, first pipe 220 and/or second pipe 230 may include or be coupled or connect to one or more flanges 208. For example, a flange (e.g., 208) may be positioned at an end of a pipe to connect the pipe (e.g., 220, 230) to another component, such as one other pipe. For example, as depicted in FIG. 2A, a first flange (e.g., 208) may be positioned between orifice 240 and first end 222 of first pipe 220. Additionally, or alternatively, a second flange (e.g., 208) may be positioned between second end 234 and reactor piping 258 of an inlet (e.g., 102).

In some implementations, first pipe 220 may include a taper at one end (e.g., 222). To illustrate, first pipe 220 may be tapered such that a dimension, such as a diameter, of channel 226 increased from first end 22 to second end 224. For example, channel 226 of first pipe 220 increases in cross-sectional area as channel 226 extends from the first inlet (e.g., 222) to the first outlet (e.g., 224). Accordingly, first pipe 220 may increase in cross-sectional area as the first pipe (e.g., channel 226) extends from first end 222 to second end 224. In this way, a fluid (e.g., hydrocarbon feed) may decrease in velocity as the fluid travels from first end 222 to second end 224 of first pipe 220.

Second pipe 230 may include a first end 232, a second end 234, a channel 236, and a bend 238. As shown, second pipe 230 extends from first end 232 to second end 234. First end 232 and second end 234 may include or correspond to first end 132 and second end 134, respectively. As shown channel 236 extends between first end 232 and second end 234 to convey fluid from 232 first end to second end 234. Channel 236 may include or correspond to channel 136. As shown, second pipe 230 is in fluid communication with first pipe 220. For example, first end 232 of second pipe 230 may be coupled to second end 224 of first pipe 220 to define at least a portion of the flow path of assembly 210a, 210b. In some implantations, second pipe 230 is coupled (e.g., directly or indirectly) to a reactor (e.g., 150). To illustrate, the flow path of the system may be defined from first pipe 220, through second pipe 230, to an inlet (e.g., port) of a reactor (e.g., 150).

Second pipe 230 includes a second distance D2 that defines a transverse dimension, such as a maximum transverse dimension of channel 236 taken along a plane orthogonal the longitudinal axis of channel 236. D2 may be measured from opposing sides of inner surface of pipe 230. In some implementations, D2 corresponds to an inner diameter of channel 236.

Bend 238 may correspond to a portion of second pipe 230 that is curved or angled. Bend 238 may include a corner (e.g., an edge) or a smooth corner (e.g., a curve) that creates an oblique shock within fluid flowing through second pipe 230. Referring to FIG. 2B, bend 238 may include a first portion 250 of second pipe 230 that extends along a first longitudinal axis 251 and a second portion 252 that extends along a second longitudinal axis 253 that is angularly disposed relative to the first longitudinal axis. In some implementations, first longitudinal axis 251 is angularly disposed relative to the second longitudinal axis by an angle 254. In some implementations, angle 254 is greater than or equal to any of, or between any two of, the following: 20, 30, 40, 50, 60, 70, or 80 degrees (°) (e.g., between 20 and 45.5°). Bend 238 may also include a transition portion 256, such as a curved portion, connecting the first portion 250 to second portion 252. To illustrate, transition portion 256 may include a portion of second pipe 230 that includes a curved portion (or an edge) that transitions from first portion 250 to second portion 252. In some implementations, transition portion 256 may include a deflection angle (e.g., angle 254) that is less than 60° (e.g., 45.5°) or angle of the standard Long radius elbow. In some implementations, second pipe may include an elbow pipe (e.g., 45° short radius or 45° long radius). Although aspects of bend 238 have been described with reference to FIG. 2B, such aspects may be included in assembly 210a of FIG. 2A. As second pipe 230 may be positioned just upstream of a reactor (e.g., 150), fluid exiting the second pipe may expand into a large chamber of the reactor. Bend 238 may induce an oblique shock in the fluid based on angle 254 to restore an effective pressure ratio of the system. In this manner, inlet assembly may operate with increased efficiency Referring to FIGS. 2A-2B, orifice 240 may include a body 242 that defines an aperture 244 through which fluid may travel. Body 242 may be coupled to first pipe 220 and/or second pipe 230 to restrict flow of a fluid within the flow path of assembly 210a, 210b. In some implementations, body 242 may be coupled to flange 208. Orifice 240 may be sized and shaped such that that flow of fluid through aperture 244 will induce sonic flow (e.g., choked flow) in the fluid. For example, orifice 240 is configured to attain sonic flow at a percentage of startup feed flow of the system. To illustrate, orifice 240 may configured to attain sonic flow of at least 75% (e.g., 80%) of startup feed flow of the system, as an illustrative, non-limiting example. In this way, orifice 240 may generate post sonic operation in normal operating conditions of a reactor (e.g., 150), allowing uniform feed distribution through the entire operating range of the system.

In some implementations, orifice 240 may define a single aperture (e.g., 244) having a third distance D3 that defines a maximum transverse dimension of aperture 244. In some implementations, D3 corresponds to a diameter of aperture 244. To illustrate, orifice 240 may define an orifice plate (e.g., concentric, eccentric, segmental, quadrant edged, square edged, conical, or the like). In some implementations, distance D3 is greater than or equal to any of, or between any two of, the following: 300, 310, 320, 340, 350, 360, 370, 380, 390, 400, 410, 420, 430, 440, or 450 millimeters (mm) (e.g., between 350 and 406 mm). Distance D3 may include a vena-contracta of assembly 210a, 210b. To illustrate, distance D3 (e.g., maximum transverse dimension of aperture 244) is less than the minimum transverse dimension of channel 226 of first pipe 220 and the minimum transverse dimension of channel 236 of pipe 230. Aperture 244 may be sized to a dimension such that orifice 240 may induce sonic flow at less than a percentage (e.g., 95%) of start-up flow of the system. In this way, orifice 240 may be selected based on operational system parameters (e.g., fluid, number of reactors, velocity of fluid, desired flow rate, etc.). In other implementations, orifice body 242 may define a plurality of apertures to induce sonic flow.

Referring to FIG. 2A, orifice 240 may be positioned upstream of first pipe 220. For example, orifice 240 may be coupled or connected to first end 222. In this way, fluid traveling through first pipe 220 may be controlled without regard to pressure variations downstream of first pipe 220. To illustrate, orifice 240 may define a vena-contracta of assemble 210a to induce sonic flow in a fluid travelling through first pipe 220. In other implementations, orifice 240 may be coupled between first end 222 and second end 224 within channel 226 of first pipe 220.

Referring now to FIG. 2B, orifice 240 may be positioned downstream of end 222 of pipe 220. For example, orifice 240 may be interposed between pipe 220 and pipe 230 such that fluid attains sonic flow within channel 236 of pipe 230 during operation of the system. To illustrate, orifice 240 may be coupled or connected to end 224 of pipe 220 and/or end 232 of pipe 230. In such implementations, fluid may regain pressure while traveling through pipe 230 to minimize the pressure drop due to orifice 240. In some implementations, bend 238 of second pipe may cause a sonic fluid to from a plurality of waves (e.g., expansion fans) upon passing bend 238 such that the pressure of the sonic fluid increases as it travels through second pipe 230.

Positioning orifice 240 at second end 224 of first pipe 220 and/or first end 232 of second pipe 230 allows mass flow of fluid leads to a lower pressure drop of the fluid. Consequently, the velocity of the fluid may decrease from the lower pressure drop. As explained above, with reference to FIG. 1, a decrease in conversion from a lower pressure drop of a fluid may be overcome by an increase in compressor (e.g., 105) capability and the increase in compressor suction pressure may outweigh the drop in conversion up to a certain point (e.g., stonewall limit). When orifice 240 is positioned closer to first end 222 of first pipe 220 than to second end 224, the pressure drop and velocity of fluid through the reactor (e.g., 150) may be increased. Accordingly, orifice 240 may be positioned relative to first end 222 of first pipe 220, second end 224 of the first pipe, first end 232 of second pipe 230, bend 238 of the second pipe, or other feature to maximize efficiency of the system based on a compressor-type and/or a reactor-type. While each of first pipe 220 and second pipe 230 are described and depicted as separate components, it should be known that first pipe 220 and second pipe 230 of system may be unitary such that pipe 220 corresponds to a first portion of a pipe and pipe 230 corresponds to a second portion of the pipe.

In some implementations, an inlet assembly (e.g., 210a, 210b), such as a multi-section pipe, includes a first pipe section (e.g., 220) and a second pipe section (e.g., 230). The first pipe section defines a first channel 226 configured to convey fluid from a first inlet (e.g., 222) of the first pipe section to a first outlet (e.g., 224) of the first pipe section. The second pipe section (e.g., 230) defines a second channel 236 configured to convey the fluid from a second inlet (e.g., 232) of the second pipe section to a second outlet (e.g., 234) of the second pipe section. In some such implementations, the second pipe section 230 includes a first portion 250 extending along a first longitudinal axis 251, a second portion 252 extending along a second longitudinal axis 253 that is angularly disposed relative to the first longitudinal axis 251, and an interface portion (e.g., 238) connecting the first portion 250 to the second portion 252. Orifice plate 240 may be positioned at the first inlet (e.g., 222) or the first outlet (e.g., 224). For example, orifice (e.g., 240) may be coupled to the first inlet. In other implementations, orifice (e.g., 240) may be coupled to the first outlet. In some implementations, orifice plate 240 includes a maximum transverse dimension that is less than a minimum transverse dimension of each of the first and second channels 226, 236.

The interface portion (e.g., 238) of the second pipe section (e.g., 230) includes a deflection angle 254 that is less than a particular angle, such as less than 60 degrees (e.g., 45.5 degrees) or angle of the standard Long radius elbow. In some implementations, the orifice plate (e.g., 240) is positioned at the first outlet (e.g., 224). The inlet assembly may be coupled to a dehydrogenation reactor (e.g., 150). In such implementations, the multi-section pipe is positioned upstream of the dehydrogenation reactor such that a flow path is defined from the first pipe section (e.g., 220), through the orifice plate (e.g., 240), through the second pipe section (e.g., 230), to an inlet of the dehydrogenation reactor. The first pipe section (e.g., 220) and the second pipe section (e.g., 230) may include a hot-wall pipe. Additionally, or alternatively, the first pipe section (e.g., 220) may be tapered such that the first channel (e.g., 226) increases in cross-sectional area as the first channel extends from the first inlet (e.g., 222) to the first outlet (e.g., 224).

Figure 3:
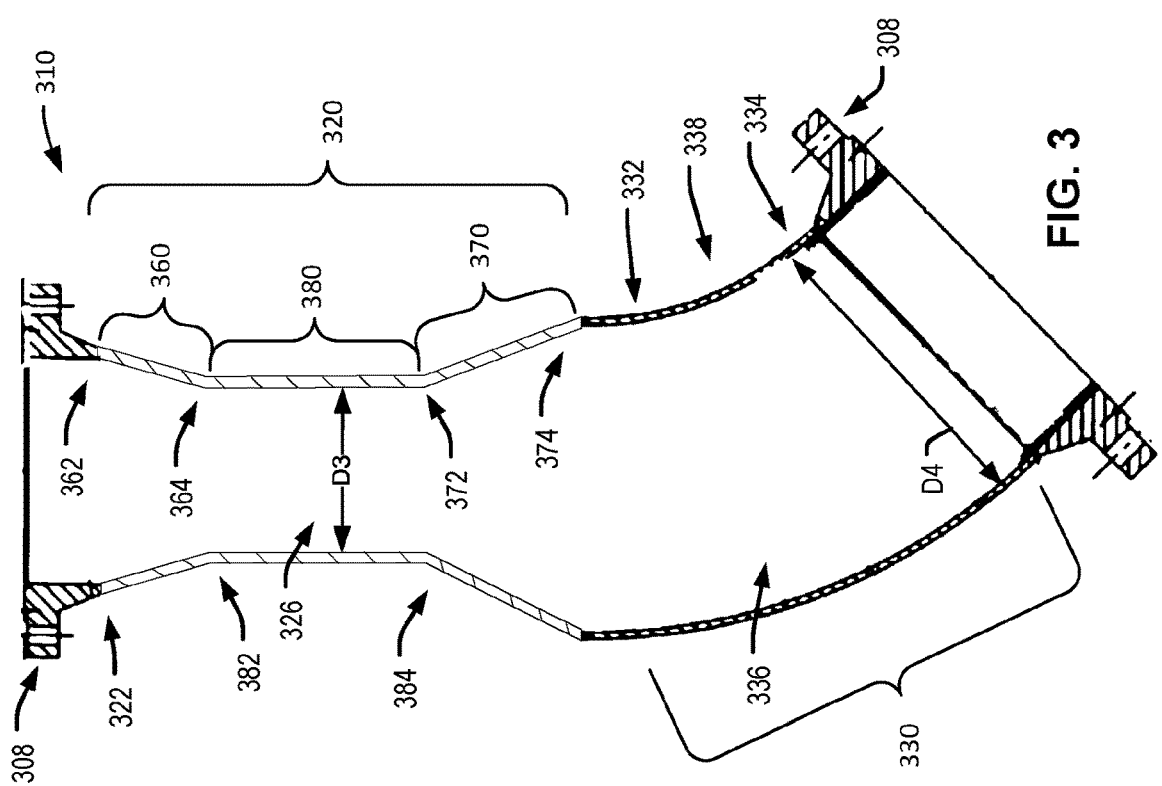
FIG. 3 is a cross-sectional view of another example of an inlet assembly.

Referring now to FIG. 3, a cross-sectional view of an example of inlet assembly 310 of a dehydrogenation system is shown. The system may include or correspond to one or more components of system 100. For example, inlet assembly 310 may include or correspond to assembly 110, 210. As shown, assembly 310 includes a first pipe 320, a second pipe 330, which may include or correspond to first pipe 120, 220 and second pipe 130, 230; respectively.

First pipe 320 may include a first end 322, a second end 324, and a channel 326. As shown first pipe 320 may extend from end 322 to end 324 to define channel 326. Additionally, first pipe 320 includes one or more portions, such as, a nozzle portion 360, a divergent portion 370, and a throat portion 380. Nozzle portion 360, divergent portion 370, and throat portion 380 each define a portion of first pipe 320 between end 322 and end 324. In some implementations, nozzle portion 360, divergent portion 370, and throat portion 380 are unitary such that the components define a flow path of first pipe 320. In other implementations, nozzle portion 360, divergent portion 370, and throat portion 380 may be coupled together in any suitable manner to define the flow path of first pipe 320. In some implementations, first pipe 320 and/or second pipe 330 may include one or more flanges 308 positioned at an end (e.g., 322, 324, 332, 334) of the pipe to connect the pipe to another component (e.g., reactor piping, a port, or a reactor, etc.).

Nozzle portion 360 includes an upstream end 362 and a downstream end 364. As shown, nozzle portion 360 is shaped (e.g., tapered) such that a fluid may increase in pressure as it travels from upstream end 362 to downstream end 364. For example, a diameter of channel 326 at upstream end 362 is greater than a diameter (e.g., D3) of the channel at downstream end 364. To illustrate, nozzle portion 360 may include a frustoconical portion of first pipe 320. In some implementations, upstream end 362 includes or corresponds to first end 322 of first pipe 320; however, in other implementations, the upstream end of nozzle portion 360 is downstream of the first end of first pipe. As shown, nozzle portion 360 may, but need not, be coupled to flange 308.

Divergent portion 370 includes an upstream end 372 and a downstream end 374. As shown, divergent portion 370 extends from end 372 to end 374 to define a portion of the flow path of first pipe 320. Divergent portion 370 may be shaped (e.g., tapered) such that a fluid may decrease in pressure as it travels from end 372 to end 374. For example, a diameter (e.g., D3) of channel 326 at end 372 is less than a diameter of the channel at end 374. In some implementations, divergent portion 370 the decrease in diameter of channel 326 from upstream end 372 to downstream end 374 is linear (e.g., decreases at a constant rate). To illustrate, divergent portion 370 may include a frustoconical portion of first pipe 320. In some implementations, divergent portion 370 (e.g., diffuser) is positioned downstream of nozzle portion 360. To illustrate, a flow path of first pipe 320 may flow from nozzle portion 360 to divergent portion 370. In some implementations, downstream end 374 includes or corresponds to second end 324 of first pipe 320; however, in other implementations, the downstream end of divergent portion 370 is upstream of the second end of the first pipe. In the foregoing implementations, fluid may regain pressure while traveling through divergent portion 370 to minimize thermodynamic drop in the system.

In some implementations, a length of divergent portion 370 (e.g., from end 372 to end 374) is less than a length of nozzle portion 360 (e.g., from end 362 to end 364). In this way, regaining of pressure from divergent portion 370 may be reasonably restricted to correspond to the suction pressure of a compressor's limit (e.g., stonewall limit). For example, divergent portion may be any suitable length such that pressure regain corresponds to maximum efficiency while a compressor is operating at the stonewall limit (e.g., choke limit).

Throat portion 380 includes an upstream end 382 and a downstream end 384. As shown, throat portion 380 extends from upstream end 382 to downstream end 384 to define a portion of the flow path of first pipe 320. In some implementations, throat portion 380 in cylindrical. For example, a diameter (e.g., D3) of channel 326 may be constant from upstream end 382 to downstream end 384 of throat portion 380. However, in some implementations, throat portion may be tapered (e.g., by less than 4.2 degrees) from upstream end 382 (toward downstream end 384) or from downstream end 384 (toward upstream end 382). Throat portion 380 may define a length measured from upstream end 382 to downstream end 384 that is greater than or equal to a length, such as a length greater than or equal to 700 millimeters (mm) (e.g., 740 mm). However, throat portion 380 may be any suitable length such that the boundary layer of a fluid flowing through first pipe 320 is contained within the throat portion and critical flow occurs.

In some implementations, throat portion 380 is positioned downstream from nozzle portion 360. In this way, throat portion 380 may ensure critical flow of fluid by maintaining the boundary layer of the fluid. Throat portion 380 may be interposed between nozzle portion 360 and divergent portion 370. For example, upstream end 382 of throat portion 380 may be coupled to, or correspond to, downstream portion (e.g., 364) of nozzle portion 360. Additionally, or alternatively, downstream end 384 of throat portion 380 may be coupled to, or correspond to, upstream portion (e.g., 372) of divergent portion 370. In some such implementations, a diameter of channel 326 at downstream end 364 of nozzle portion 360 is substantially equal to a diameter of the channel 326 at throat portion 380 (e.g., at upstream end 382). In some implementations, first pipe 320 defines a flow path from the first end 322, through the nozzle portion 360, through the throat portion 380, through the divergent portion 370, and to the second end 324. In this way, an orifice (e.g., 140, 240) is not required to create sonic flow within assembly 310. However, in some implementations, assembly 310 may include an orifice based on specific application of system 300. In implementations of assembly 310 that include an orifice, orifice may be sized and positioned in a manner similar to orifice 140, 240.

Example

As an illustrative example, Table 1 (below) shows that first pipe 320 may be used in place of orifice 240 to produce an equal mass flow of the system.

TABLE 1

|  | A1 Assembly 210 | A2 Assembly 310 | B1 Assembly 210 | B2 Assembly 310 | C1 Assembly 210 | C2 Assembly 310 |
| --- | --- | --- | --- | --- | --- | --- |
| MW (KG/KGMOL) | 58 | 58 | 58 | 58 | 58 | 58 |
| CP/CV | 1.041 | 1.041 | 1.041 | 1.041 | 1.041 | 1.041 |
| P UPSTREAM (KGF/CM2A) | 1.18 | 1.18 | 1.18 | 1.18 | 1.18 | 1.18 |
| TEMP (° C.) | 627 | 627 | 627 | 627 | 627 | 627 |
| DIAMETER (MM) | 370 | 320 | 406 | 352 | 438 | 379 |
| MASS FLOW (KG/HR) | 57574.63 | 57574.63 | 69323.39 | 69323.39 | 80737.14 | 80737.14 |

In Table 1, the mass flow of a fluid through an inlet assembly (e.g., 110, 210a, 210b, 310). As shown, the physical properties of the fluid are constant for each test and a minimum diameter of the inlet assembly is different. As shown in case A1 and A2, both inlet assembly 210 and inlet assembly 310 may be used to obtain a mass flow by changing a diameter of the respective inlet assemblies. To illustrate, in case A2 diameter D3 of throat portion 380 is 320 millimeters to generate a mass flow of 57,574.63 (kg/hr) and in case A1 diameter D3 of orifice 240 is 370 millimeters to generate the same mass flow. Cases B1 and B2, diameter D3 of inlet assemblies 210, 310 may be modified to increase the mass flow through each inlet assembly, demonstrating the range of mass flux variations possible in identical system due to various aspects related to flow balancing distribution. As shown, increasing diameter D3 results in an increased mass flow rate. Cases C1 and C2 illustrate an optimal flow rate for a particular dehydrogenation process and show that each system can be customized based on a desired operational system parameter.

End Example

Second pipe 330 may include a first end 332, a second end 334, a channel 336, and a bend 338. As shown, second pipe 330 extends from first end 332 to second end 334 to define channel 336 configured to convey fluid within the second pipe 330. First end 332, second end 334, and channel 336 may include or correspond to first end 132, 232; second end 134, 234; and channel 136, 236, respectively. As shown, second pipe 330 is in fluid communication with first pipe 320. Second pipe 330 may include a bend 338 such that second pipe 330 is curved or angled. Bend 338 may include or correspond to bend 238. While each of first pipe 320 and second pipe 330 are described and depicted as separate components, in some implementations, first pipe 320 and second pipe 330 may be unitary such that first pipe 320 corresponds to a first portion of a pipe and second pipe 330 corresponds to a second portion of the pipe. In some implementations, second pipe 330 may, but need not be, coupled to a flange 308.

In some implementations, a system includes a multi-section pipe including a first pipe section (e.g., 320) and a second pipe section (e.g., 330). The first pipe section defines a first channel 326 configured to convey fluid from a first inlet (e.g., 322) of the first pipe section to a first outlet (e.g., 324) of the first pipe section. The second pipe section defines a second channel 336 configured to convey fluid from a second inlet (e.g., 332) of the second pipe section to a second outlet (e.g., 334) of the second pipe section. In some such implementations, the second pipe section includes a first portion extending along a first longitudinal axis, a second portion extending along a second longitudinal axis that is angularly disposed relative to the first longitudinal axis, and a connecting portion configured to connect the first portion to the second portion.

In some implementations, the connecting (e.g., 338) of the second pipe section (e.g., 330) includes a deflection angle that is less than 60 degrees. The multi-section pipe (e.g., 310) may be positioned upstream of a dehydrogenation reactor (e.g., 150) such that a flow path is defined from the first pipe section (e.g., 320), through the second pipe section (e.g., 330), to an inlet (e.g., 152) of the dehydrogenation reactor.

In some implementations, the first pipe section (e.g., 320) includes a hot-wall pipe and/or the second pipe section (e.g., 330) includes a hot-wall pipe. Additionally, or alternatively, the first pipe section (e.g., 320) may be tapered such that the first channel (e.g., 326) increases in cross-sectional area as the first channel extends from the inlet (e.g., 322) to the outlet (e.g., 324).

In some implementations, a system include a multi-section pipe (e.g., 310) that includes first pipe 320 having an inlet (e.g., 322) and an outlet (e.g., 324) and defining channel 326 configured to convey fluid from the inlet to the outlet to define a flow path of the first pipe. First pipe 320 includes nozzle portion 360, divergent portion 370, and throat portion 380. In some implementations, nozzle portion 360 extends from the inlet (e.g., 322) and includes a taper that decreases a cross-sectional area of channel 326 from an upstream end (e.g., 362) of nozzle portion 360 to a downstream end (e.g., 364) of nozzle portion 360. Divergent portion 370 extends from the outlet (e.g., 324) and includes a taper that increases the cross-sectional area of channel 326 from an upstream end (e.g., 372) of divergent portion 370 to a downstream end (e.g., 374) of divergent portion 370. Throat portion 380 extends between the downstream end (e.g., 364) of nozzle portion 360 and the upstream end (e.g., 372) of divergent portion 370. Additionally, second pipe 330 may be in fluid communication with first pipe 320.

In some implementations, an inner diameter of channel 326 at throat portion 380 is substantially equal to the inner diameter of channel 326 at the downstream end (e.g., 364) of nozzle portion. Additionally, or alternatively, first pipe 320 and second pipe 330 include a hot-wall pipe. In some of the foregoing implementations, a distance between the inlet (e.g., 322) of first pipe 320 and a reactor (e.g., 150) is between 10-15 meters. Some implementations include a plurality of dehydrogenation reactors arranged in parallel and in communication with the multi-section pipe (e.g., 310). In some implementations, second pipe 230 includes an elbow pipe with a deflection angle that is less than or equal to 50 degrees.

Figure 4B:
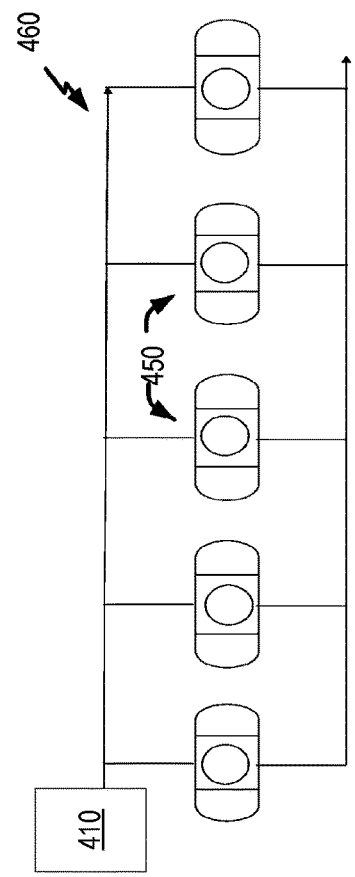

Referring now to FIGS. 4A-4B, aspects of one or more components of a dehydrogenation system 400 are shown. FIG. 4A shows an illustrative diagram of an example of a non-balanced dehydrogenation assembly 400, and FIG. 4B shows an illustrative diagram of a second example of a balanced dehydrogenation assembly 460. System 400, 460 may include or correspond to one or more components of dehydrogenation system 100.

Each of systems 400, 460 include an inlet assembly 410 and one or more reactors 450. Assembly 410 and reactors 450 may include or correspond to assembly 110, 210, 310 and reactor 150, respectively. As shown, assembly 410 (e.g., inlet manifold) may be positioned upstream from a plurality of dehydrogenation reactors 450. Assembly 410 may control the flow rate of a fluid flowing into each of the reactors 450. To illustrate, the flow rate of fluid may be controlled upstream of assembly 410 to evenly distribute flow to each of the reactors 450 of system 400, 460.

Energy conserved by inlet assembly 410 may cause distribution of fluid to dehydrogenation reactors 450 to vary. Accordingly, catalyst usage and temperature profiles of one dehydrogenation reactor (e.g., 450) may vary relative to one other dehydrogenation reactor (e.g., 450) of system 400, 460; however, the increased efficiency of system may outweigh issues associated with flow distribution. For example, a suction pressure of a driver (e.g., compressor, pump, or the like) can be optimized by reducing the pressure drop within inlet assembly 410, as described herein, to increase the efficiently and energy conservation of dehydrogenation system 400, 460. In this way, inlet assembly 410 may minimize thermodynamic loss and decrease cost of operation with increased efficiency. Accordingly, inlet assembly 410 may be configured to provide improved energy efficiency for pipe flow in dehydrogenation system 400, 460.

As shown in FIGS. 4A-4B, dehydrogenation reactors 450 may be arranged in parallel. In some implementations, dehydrogenation reactor may include or correspond to a CATOFIN® fixed bed dehydrogenation reactor. However, any other suitable reactor may be utilized in system 400, 460. While the depicted implementations shows five dehydrogenation reactors (e.g., 450), system 400, 460 may include any suitable number of reactors, such as 2, 3, 4, 5, 8, or more reactors. Inlet assembly 410 (e.g., header manifold) is positioned upstream of all of the dehydrogenation reactors 450; however in other implementations, a plurality of inlet assemblies (e.g., 410) may utilized such that an inlet assembly is positioned upstream from a respective reactor to individually control the flow of the reactors. Stated in another manner, although dehydrogenation systems 400, 460 each depict a single inlet assembly 410, in other implementations, each reactor 450 may be coupled and downstream of a corresponding inlet assembly.

Although aspects of the present implementations have been described with reference to blocks of FIGS. 1. 2A-2B, 3, and 4A-4B, it should be appreciated that operation of the implementations is not limited to the particular blocks and/or the particular order of the blocks illustrated in FIGS. 1. 2A-2B, 3, and 4A-4B. Accordingly, aspects described herein may provide functionality as described herein using various blocks in a sequence different than that of FIGS. 1. 2A-2B, 3, and 4A-4B. The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

Referring now to FIG. 5, a method 500 of operating a dehydrogenation system is shown. Method 500 may be performed at, by, or with system 100, or one or more components, such as inlet assembly 110, 210a, 210b, 310, or 410. For example, method 500 may include operating a dehydrogenation system having an inlet assembly 110, 210a, 210b, 310, or 410 and a reactor 150.

Method 500 includes receiving, by a first pipe, a fluid having hydrogen, at 502. First pipe may include or correspond to first pipe 120, 220, 320. For example, first pipe may include a nozzle portion, a diffuser portion, and a throat portion. In another example, first pipe may be coupled to or include an orifice, such as orifice 140, 240. Method 500 also includes reducing, by the first pipe, a pressure of the fluid, at 504. In some methods, a nozzle portion or an orifice may be utilized to reduce the pressure of the fluid. For example, reducing a pressure of the fluid may include transporting the fluid through a tapered portion of the first pipe. In some implementations, prior to reducing the pressure of the fluid by the first pipe, compressing the fluid by the first pipe.

Method 500 may include delivering, by the first pipe, the fluid to an orifice plate or a convergent-divergent nozzle, at 506. Orifice plate may include or correspond to orifice 140, 240. For example, orifice may include an orifice body and an aperture. In some implementations, delivering fluid to an orifice plate includes delivering the fluid through the aperture of the orifice. The convergent-divergent nozzle may include or correspond to nozzle portion 360, divergent portion 370, throat portion 380, or a combination thereof. Method 500 may also include inducing, by the orifice plate or the convergent-divergent nozzle, sonic flow of the fluid, at 508. For example, inducing sonic flow may include transporting the fluid through a vena contracta of the system that is defined by the orifice plate. In other implementations, a nozzle portion (e.g., the convergent-divergent nozzle) may be utilized to induce sonic flow of the fluid.

Method 500 includes receiving, by a second pipe, the fluid, at 510. Second pipe may include or correspond to second pipe 130, 230, 330. For example, second pipe may include a first end, a second end, a channel, and a bend. First end of second pipe may receive the fluid from a second end of the first pipe. In some implementations, second pipe receives the fluid in a sonic state (e.g., choked flow). Additionally, in some implementations, method 500 my include creating, by the second pipe, an oblique shock in the fluid. Method 500 includes delivering, by the second pipe, the fluid to a dehydrogenation reactor, at 512. Dehydrogenation reactor may include or correspond to dehydrogenation reactor 150. In some implementations, the fluid is delivered by the second end of the second pipe to the dehydrogenation reactor. In some implementations, delivering the fluid to the dehydrogenation reactor includes delivering the fluid to a plurality of dehydrogenation reactors disposed in parallel to each other. In such implementations, the fluid may be equally distributed to each reactor. Some implementations of method 500 may also include converting the fluid, by the dehydrogenation reactor. For example, fluid may include an alkane and some methods may include converting the alkane to an alkene, by the dehydrogenation reactor.

Although aspects of the present application and their advantages have been described in detail, it should be understood that various changes, substitutions and alterations can be made herein without departing from the spirit and scope of the disclosure as defined by the appended claims. Moreover, the scope of the present application is not intended to be limited to the particular implementations of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding implementations described herein may be utilized. Accordingly, the appended claims are intended to include within their scope such processes, machines, manufacture, compositions of matter, means, methods, or steps.

The above specification provides a complete description of the structure and use of illustrative configurations. Although certain configurations have been described above with a certain degree of particularity, or with reference to one or more individual configurations, those skilled in the art could make numerous alterations to the disclosed configurations without departing from the scope of this disclosure. As such, the various illustrative configurations of the methods and systems are not intended to be limited to the particular forms disclosed. Rather, they include all modifications and alternatives falling within the scope of the claims, and configurations other than the one shown may include some or all of the features of the depicted configurations. For example, elements may be omitted or combined as a unitary structure, connections may be substituted, or both. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one configuration or may relate to several configurations. Accordingly, no single implementation described herein should be construed as limiting and implementations of the disclosure may be suitably combined without departing from the teachings of the disclosure.

The previous description of the disclosed implementations is provided to enable a person skilled in the art to make or use the disclosed implementations. Various modifications to these implementations will be readily apparent to those skilled in the art, and the principles defined herein may be applied to other implementations without departing from the scope of the disclosure. Thus, the present disclosure is not intended to be limited to the implementations shown herein but is to be accorded the widest scope possible consistent with the principles and novel features as defined by the following claims. The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An inlet feed system for a reactor, the inlet feed system comprising:
    a multi-section pipe comprising:
        a first pipe section defining a first channel configured to convey fluid from a first inlet of the first pipe section to a first outlet of the first pipe section; and
        a second pipe section defining a second channel configured to convey fluid from a second inlet of the second pipe section to a second outlet of the second pipe section, the second pipe section including:
            a first portion extending along a first longitudinal axis;
            a second portion extending along a second longitudinal axis that is angularly disposed relative to the first longitudinal axis; and
            a curved portion connecting the first portion to the second portion; and
    an orifice plate configured to be positioned at the first inlet or the first outlet, the orifice plate includes a maximum transverse dimension that is less than a minimum transverse dimension of each of the first and second channel.

2. The system of claim 1, wherein:
the curved portion of the second pipe section comprises a deflection angle less than 60 degrees; or
the orifice plate is positioned at the first outlet; and
optionally, the first pipe section comprises a hot-wall pipe, the second pipe section comprises a hot-wall pipe, or both.

3. The system of claim 1, further comprising:
a dehydrogenation reactor; and
wherein the multi-section pipe is positioned upstream of the dehydrogenation reactor such that a flow path is defined from the first pipe section, through the orifice plate, through the second pipe section, to an inlet of the dehydrogenation reactor; or
wherein the first pipe section is tapered such that the first channel increases in cross-sectional area as the first channel extends from the first inlet to the first outlet.

4. A method of performing a dehydrogenation process by using the system of claim 1, the method comprising:
receiving, by the first pipe, a fluid having hydrogen;
reducing, by the first pipe, a pressure of the fluid;
delivering, by the first pipe, the fluid to the orifice plate or a convergent-divergent nozzle;
inducing, by the orifice plate or the convergent-divergent nozzle, sonic flow of the fluid;
receiving, by the second pipe, the fluid;
delivering, by the second pipe, the fluid to a dehydrogenation reactor.

5. The method of claim 4, further comprising:
prior to reducing the pressure of the fluid by the first pipe, compressing the fluid by the first pipe; or
creating, by the second pipe, an oblique shock in the fluid.

6. The method of claim 4, wherein:
delivering the fluid to the dehydrogenation reactor comprises delivering the fluid to a plurality of dehydrogenation reactors disposed in parallel; or
the fluid comprises an alkane and the method further comprising converting the alkane to an alkene, by the dehydrogenation reactor.

7. The method of claim 4, wherein:
delivering the fluid to the dehydrogenation reactor comprises delivering the fluid to a plurality of dehydrogenation reactors disposed in parallel; or
the fluid comprises an alkane and the method further comprising converting the alkane to an alkene, by the dehydrogenation reactor.

* * * * *